(12) United States Patent
Schoenefeld et al.

(10) Patent No.: US 7,455,726 B2
(45) Date of Patent: Nov. 25, 2008

(54) PHOTOSTABILISED EFFECT PIGMENTS

(75) Inventors: Ulrich Schoenefeld, Bickenbach (DE); Padma Kaviratna, Pooler, GA (US)

(73) Assignee: Merck Patent GmbH, Darmstadt (DE)

( * ) Notice: Subject to any disclaimer, the term of this patent is extended or adjusted under 35 U.S.C. 154(b) by 252 days.

(21) Appl. No.: 10/557,476

(22) PCT Filed: Apr. 27, 2004

(86) PCT No.: PCT/EP2004/004418

§ 371 (c)(1), (2), (4) Date: Nov. 21, 2005

(87) PCT Pub. No.: WO2004/104110

PCT Pub. Date: Dec. 2, 2004

(65) Prior Publication Data

US 2007/0060668 A1 Mar. 15, 2007

Related U.S. Application Data

(60) Provisional application No. 60/472,138, filed on May 21, 2003.

(51) Int. Cl.
*C09C 1/00* (2006.01)
*C09C 1/36* (2006.01)
*C09C 3/06* (2006.01)
*C09D 11/02* (2006.01)
*C09D 5/36* (2006.01)
*C01G 23/047* (2006.01)
*A61K 8/00* (2006.01)

(52) U.S. Cl. .................. 106/479; 106/31.65; 106/31.9; 106/415; 106/426; 106/428; 106/429; 106/436; 106/438; 106/442; 106/444; 106/445; 106/446; 106/447; 106/451; 106/466; 106/467; 106/471; 47/57.6; 162/162; 424/69; 427/215; 427/218; 428/403; 428/404; 501/32; 524/408

(58) Field of Classification Search .................. 106/451, 106/479, 415, 426, 428, 429, 438, 442, 444, 106/445, 446, 447, 466, 467, 471, 31.65, 106/31.9, 436; 47/57.6; 162/162; 424/69; 427/215, 218; 428/403, 404; 501/32; 524/408
See application file for complete search history.

(56) References Cited

U.S. PATENT DOCUMENTS

| | | | |
|---|---|---|---|
| 3,087,828 A | | 4/1963 | Linton et al. |
| 3,087,829 A | * | 4/1963 | Linton ........................ 106/417 |
| 3,981,737 A | * | 9/1976 | Evilampi et al. ............ 106/425 |
| 5,766,335 A | | 6/1998 | Bonnard et al. |
| 5,853,955 A | * | 12/1998 | Towfiq .................. 430/270.12 |
| 5,855,660 A | | 1/1999 | Bonnard et al. |
| 5,958,125 A | | 9/1999 | Mronga et al. |
| 6,719,838 B2 | * | 4/2004 | Heider et al. ............... 106/417 |

FOREIGN PATENT DOCUMENTS

| | | |
|---|---|---|
| GB | 974874 | 11/1964 |
| JP | 03044949 B2 | 5/2000 |

OTHER PUBLICATIONS

Database WPI Section Ch, Week 200029 Derwent Publications Ltd., London, GB: AN 1994-148095, XP002298942, May 2000.
English Translation of JP 03044949, May 2000.

* cited by examiner

*Primary Examiner*—Anthony J Green
(74) *Attorney, Agent, or Firm*—Millen, White, Zelano & Branigan, P.C.

(57) ABSTRACT

The present invention relates to photostabilised effect pigments in which one or more calcined and vanadium-containing oxide layers, alone or mixed with sulfates, borates or phosphates, have been applied to a substrate, to a process for the preparation thereof, and to the use thereof in plastics, paints, coatings, printing inks, cosmetics, films, in security printing, for laser marking, in thermal protection or for colouring seed.

20 Claims, No Drawings

PHOTOSTABILISED EFFECT PIGMENTS

This application is a 371 of PCT/EP04/004418,filed Apr. 27, 2004,which claims the benefit of U.S. Provisional Application No. 60/472,138, filed May 21, 2003.

The present invention relates to photostabilised effect pigments in which one or more calcined and vanadium-containing oxide layers, alone or mixed with sulfates, borates or phosphates, have been applied to a substrate, to a process for the preparation thereof, and to the use thereof in plastics, paints, coatings, printing inks, cosmetics, films, in security printing, for laser marking, in thermal protection or for colouring seed.

Plastic parts and surface-coating layers for outdoor applications are often subjected to extreme weather conditions and long-lasting, intense exposure to light over an extended time, resulting in ageing of the materials. This is evident from discolouration, embrittlement and reduced mechanical and chemical stability. The causes thereof are oxidative or photolytic decomposition of the binders or decomposition due to the action of water in liquid form or water vapour. In addition, the pigments employed, in particular pearlescent pigments comprising titanium oxide layers, may also impair the resistance of the application media to the influences of light and weathering. The reason for this lies in the particular photoactivity of titanium dioxide layers, which accelerates photolytic decomposition of the organic constituents of the application medium.

In order to inhibit these ageing processes, stabilisers, for example UV light-absorbing substances, are added to formulations for outdoor applications. Furthermore, the pigments may be provided with additional inorganic layers. Thus, WO 98/58017 describes a composition comprising a polyolefin, an antioxidant and a pearlescent pigment which is said to exhibit a lower tendency towards yellowing. The antioxidant here is an essential constituent of the mixture, which restricts the usability in application media since the antioxidant must be matched to the other application constituents in order to avoid destruction of these compounds in the applications.

The increase in the photostability of titanium dioxide pigments through the addition of dopants has long been known. Thus, DE 2 407 429 describes the precipitation of vanadium compounds onto titanium dioxide pigment suspensions, where the pigment must not be calcined under any circumstances in order to prevent the formation of coloured compounds or subsequent darkening of the pigment. However, uncalcined pigments are distinguished by lower stability, which is particularly disadvantageous in applications with a long service life, such as, for example, surface coatings or plastics.

From DE 2 545 243 is a process for the preparation of a titanium dioxide pigment having increased photochemical stability by addition of metal ions from the group of vanadium, copper and/or manganese to water-containing titanium dioxide, followed by calcination at 600 to 1100° C. This process is restricted to pure titanium dioxide pigments, which restricts the range of applications for paints, coatings or plastics.

The object was therefore to provide photostabilised effect pigments having improved applicational properties which can be employed without restriction in all common application media and applications without exhibiting changes in the properties of the effect pigments. In addition, the photostabilised effect pigments should be easily and inexpensively accessible, i.e. they should be easy and inexpensive to prepare.

This complex object is achieved in accordance with the present invention by a photostabilised effect pigment in which one or more calcined and vanadium-containing oxide layers, alone or mixed with sulfates, borates or phosphates, have been applied to a substrate.

The effect pigments according to the invention are distinguished by improved photostability, are easily accessible and can be incorporated into all conceivable application media and applications. They are chemically stable and inert and exhibit the usual features for effect pigments, such as, for example, lustre, tinting strength or colour variety, in combination with the photostability. In addition, the pigments according to the invention can be prepared in a simple process with a broad choice of substrates, it being possible, depending on the embodiment, to integrate the process for the preparation of the pigments according to the invention directly into the process for the preparation of the effect pigments. This means lower equipment complexity and allows better control of the desired pigment properties, such as, for example, lustre, colour or hiding power. The use of the pigments according to the invention enables the addition of further photostabilisers to formulations or applications to be reduced or even omitted entirely, which likewise reduces the complexity and/or cost of preparation of these formulations and applications.

The effect pigments according to the invention are based on substrates, which can have any regular or irregular shape. In a preferred embodiment, the substrate consists of a flake-form, spherical or needle-shaped support and/or a flake-form, spherical or needle-shaped support coated with one or more transparent, semitransparent and/or opaque layers comprising metal oxides, metal oxide hydrates, metal suboxides, metals, metal fluorides, metal nitrides, metal oxynitrides or mixtures of these materials. Particular preference is given to the use of substrates based on flake-form supports. Suitable are, for example, flake-form $TiO_2$, synthetic or natural mica, glass flakes, metal flakes, flake-form $SiO_2$, $Al_2O_3$ or flake-form iron oxide. The metal flakes can consist, inter alia, of aluminium, titanium, bronze, steel or silver, preferably aluminium and/or titanium. The metal flakes here may be passivated by corresponding treatment. In a preferred embodiment, the support may be coated with one or more transparent, semitransparent and/or opaque layers comprising metal oxides, metal oxide hydrates, metal suboxides, metals, metal fluorides, metal nitrides, metal oxynitrides or mixtures of these materials. The metal oxide, metal oxide hydrate, metal suboxide, metal, metal fluoride, metal nitride, metal oxynitride layers or the mixtures thereof can be of low (refractive index <1.8) or high refractive index (refractive index ≧1.8). Suitable metal oxides and metal oxide hydrates are all metal oxides or metal oxide hydrates known to the person skilled in the art, such as, for example, aluminium oxide, aluminium oxide hydrate, silicon oxide, silicon oxide hydrate, iron oxide, tin oxide, cerium oxide, zinc oxide, zirconium oxide, chromium oxide, titanium oxide, in particular titanium dioxide, titanium oxide hydrate, and mixtures thereof, such as, for example, ilmenite or pseudobrookite. Metal suboxides which can be employed are, for example, the titanium suboxides. Suitable metals are, for example, chromium, aluminium, nickel, silver, gold, titanium, copper or alloys, a suitable metal fluoride is, for example, magnesium fluoride. Metal nitrides or metal oxynitrides which can be employed are, for example, the nitrides or oxynitrides of the metals titanium, zirconium and/or tantalum. Metal oxide, metal, metal fluoride and/or metal oxide hydrate layers are preferably and metal oxide and/or metal oxide hydrate layers very particularly preferably applied to the support. It is furthermore also possible for multilayered structures comprising high- and low-refractive-index metal oxide, metal oxide hydrate, metal or metal fluoride layers to be present, preferably with high- and low-refractive-index layers alternating. Particular preference is given to layer packages comprising a high- and a low-refractive-index layer, where one or more of these layer packages may be applied to the support. The sequence of the high- and low-refractive-index layers can be matched to the support here in order to incorporate the support in the multilayered structure. In a further embodiment, the metal oxide, metal oxide hydrate, metal suboxide, metal, metal fluoride, metal nitride, metal oxynitride layers can be mixed or doped with colorants or other elements. Suitable colorants or other elements are, for example, organic or inorganic coloured pigments, such as coloured metal oxides, for example magnetite, chromium oxide or coloured pigments, such as, for example, Berlin Blue, ultramarine, bismuth vanadate, Thenard's Blue, or alternatively organic coloured pigments, such as, for example, indigo, azo pigments, phthalocyanines, or alternatively Carmine Red, or elements, such as yttrium or antimony. Besides photostability, photostabilised effect pigments comprising these layers exhibit a wide variety of colours with respect to their mass tone and may in many cases exhibit an angle-dependent change in the colour (colour flop) due to interference.

In a preferred embodiment, the outer layer on the support is a high-refractive-index metal oxide. This outer layer may additionally be on the above-mentioned layer packages or, in the case of high-refractive-index supports, be part of a layer package and may consist, for example, of $TiO_2$, titanium suboxides, $Fe_2O_3$, $SnO_2$, ZnO, $ZrO_2$, $Ce_2O_3$, CoO, $Co_3O_4$, $V_2O_5$, $Cr_2O_3$ and/or mixtures thereof, such as, for example, ilmenite or pseudobrookite. $TiO_2$ is particularly preferred.

In an embodiment which is particularly preferred in the present invention, the substrate is titanium oxide or a titanium oxide-containing substrate based on a support coated with one or more transparent, semitransparent and/or opaque layers comprising metal oxides, metal oxide hydrates, metal suboxides, metals, metal fluorides, metal nitrides, metal oxynitrides or mixtures of these materials. The outer layer of the flake-form, spherical or needle-shaped support coated with one or more transparent, semitransparent and/or opaque layers comprising metal oxides, metal oxide hydrates, metal suboxides, metals, metal fluorides, metal nitrides, metal oxynitrides or mixtures of these materials preferably comprises titanium oxide. In particular, these substrates are distinguished by high photoactivity due to the titanium oxide, which can have an adverse effect on the stability in the application medium surrounding the pigment, such as, for example, the plastic. In accordance with the present invention, such substrates can, in particular, be photostabilised, which simplifies their usability in numerous applications.

The size of the substrates is not crucial per se and depends on the shape of the substrates and on the particular area of application. Substrates based on flake-form supports and/or a flake-form support coated with one or more metal oxide, metal or metal fluoride layers generally have a thickness of between 0.05 and 5 µm, in particular between 0.1 and 4.5 µm. The length or width dimension is usually between 1 and 250 µm, preferably between 2 and 200 µm and in particular between 2 and 100 µm. Substrates comprising a spherical support and/or a spherical support coated with one or more metal oxide, metal or metal fluoride layers generally has average diameters of 10 nm to 100 µm, preferably between 500 nm and 50 µm and in particular between 1 and 20 µm.

The thickness of the metal oxide, metal oxide hydrate, metal suboxide, metal, metal fluoride, metal nitride, metal oxynitride layers or a mixture thereof is usually 3 to 300 nm and, in the case of the metal oxide, metal oxide hydrate, metal suboxide, metal fluoride, metal nitride, metal oxynitride layers or a mixture thereof, is preferably 20 to 200 nm. The thickness of the metal layers is preferably 4 to 50 nm.

Suitable for the calcined and vanadium-containing oxide layer or oxide layers applied to the substrate are the oxides of Al, Ca, Sr, Zn, Si, Zr, Ce, Ti or mixtures thereof, preferably $TiO_2$, $Al_2O_3$, $Ce_2O_3$, ZnO, $ZrO_2$ and/or $SiO_2$ are employed. Particular preference is given to the use of mixtures of the above-mentioned oxides, where ZnO is a particularly suitable mixture constituent of the oxide layer or oxide layers. Layers of these oxides are distinguished by high transparency, no or low inherent colour and high lustre, so that the colouristic properties of the substrates are not changed. Furthermore, these materials give anhydrous and chemically inert surfaces after the calcination. In the case of multicoated supports, the vanadium-containing oxide layer can be integrated into the multilayered structure, which simplifies the preparation ability. Thus, for example, the outer layer of a multilayered pigment can be a vanadium-containing titanium oxide layer, which, besides the increase in the photostability, also contributes to influencing the optical properties of the pigment, for example due to interference.

The vanadium content of the vanadium-containing oxide layer is 0.002 to 0.2% by weight, calculated as $V_2O_5$ and based on the pigment as a whole, preferably 0.01 to 0.1% by weight. The vanadium concentration in the vanadium-containing oxide layer can increase or decrease in the form of a gradient in the direction of the surface of the vanadium-containing oxide layer. The vanadium concentration in the vanadium-containing oxide layer preferably increases in the direction of the surface of the vanadium-containing oxide layer. This enables the photostability of the pigments to be increased further since the photoactivity of the pigment surface in contact with the application medium is reduced to a particularly great extent. In addition, the amount of vanadium required can be reduced in this way, which prevents a possible change in the colour and lustre properties of the pigment.

In a further embodiment, an organic coating which additionally stabilises the pigments according to the invention against further weathering influences can additionally be applied to the calcined vanadium-containing oxide layer. This enables the use of the pigments according to the invention in, for example, surface coatings for outdoor applications, which, besides photostability, also require high resistance to moisture. The organic coating applied can furthermore act as coupling reagent to the surrounding medium of the formulation or application and thus improve the applicational properties, such as, for example, the dispersibility.

The organic coating can consist of organosilanes, -aluminates, -titanates and/or -zirconates of the general formula

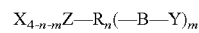

where X=OH, halogen, alkoxy, aryloxy

Z=Si, Al, Ti, Zr

R=alkyl, phenyl or hydrogen

B=organic, at least bifunctional group (alkylene, alkyleneoxyalkylene)

Y=alkyl, amino, substituted amino, hydroxyl, hydroxyalkyl, siloxane, acetoxy, isocyanate, vinyl, acryloyl, epoxide, epoxypropyloxy, imidazole or ureido group n, m=0,1,2,3 where n+m≦3.

The coupling reagents consist of an anchor group ($X_{4-n-m}Z$), which bonds to the surface, at least one hydrophobic group (R,B) and one or more functional group (Y). The coupling reagents are preferably compounds where Z=Si. The anchor group preferably consists of alkoxysilanes, which can be converted into corresponding hydroxyl groups by hydrolytic reaction conditions. The latter is able to bond to the calcined and vanadium-containing metal oxide surface and effect anchoring via oxygen bridges. In addition, it is also possible to employ mixtures of various coupling reagents, which can be applied as a mixture or individually.

The organic coating can be matched to the use medium through the choice of suitable functional groups. In addition, additional bonds between pigment and medium can be formed via the coupling reagent through reaction of the functional groups with corresponding functionalities in the application media. In a particular embodiment, the surface of the pigments according to the invention is modified by means of a combination, matched to the use medium, of organic functionalities. Also suitable for this purpose is the use of mixtures of various coupling reagents within the organic coating. The hydrophobicity of the pigment surface can be matched by integration of alkyl-containing coupling reagents, such as, for example, alkylsilanes. Besides the organosilanes, preference is also given to the use of hydro-lysates and homogeneous and heterogeneous oligomers and/or polymers thereof, which can likewise be employed alone or in combination with silanes, zirconates, aluminates, zircoaluminates and/or carboxyzircoaluminates as organic coating. Particular preference is given to an organic coating with mixtures of various coupling reagents, in particular with functional groups Y which are different from one another, which ensures a particular range of applications.

Examples of organosilanes are propyltrimethoxysilane, propyltriethoxysilane, isobutyltrimethoxysilane, n-octyltrimethoxysilane, i-octyltrimethoxysilane, n-octyltriethoxysilane, n-decyltrimethoxysilane, dodecyltrimethoxysilane, hexadecyltrimethoxysilane, vinyltrimethoxysilane, preferably n-octyltrimethoxysilane and n-octyltriethoxysilane. Suitable oligomeric, alcoholfree organosilane hydrolysates are, inter alia, the products marketed by Sivento under the trade name "Dynasylan®", such as, for example, Dynasylan HS 2926, Dynasylan HS 2909, Dynasylan HS2907, Dynasylan HS 2781, Dynasylan HS 2776, Dynasylan HS 2627. In addition, oligomeric vinylsilane and also aminosilane hydrolysate are suitable as organic coating. Functionalised organosilanes are, for example, 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane, 1,3-bis(3-glycidoxypropyl)-1,1,3,3,-tetramethyldisiloxane, ureidopropyltriethoxysilane, preferably 3-aminopropyltrimethoxysilane, 3-methacryloxytrimethoxysilane, 3-glycidyloxypropyltrimethoxysilane, beta-(3,4-epoxycyclohexyl) ethyltrimethoxysilane, gamma-isocyanatopropyltrimethoxysilane. Examples of polymeric silane systems are described in WO 98/13426 and marketed, for example, by Sivento under the trade name Hydrosil®.

The organic coating has a positive influence on the surface properties of the calcined vanadium-containing oxide layers. The surfaces post-coated with the organic coating are more hydrophobic and less polar than the un-treated oxide surfaces and can thus be wetted better by binders and organic solvents. This results in better compatibility of the pigments according to the invention with the binder systems used in the application, in particular surface coatings. Furthermore, the organic coating, owing to its steric screening of the pigment surface, inhibits agglomeration of the pigment particles and thus improves their dispersibility.

The object of the present invention is furthermore achieved by a process for the preparation of photostabilised effect pigments in which one or more vanadium-containing hydroxide, oxide hydrate and/or oxide layers, alone or mixed with sulfates, phosphates and/or borates, are applied to a substrate, and the resultant pigment is subsequently calcined. The process according to the invention can be carried out in a one-step production process and is thus inexpensive and simple. In the case of multilayered substrates, the process according to the invention can be incorporated directly into the production process of the pigment.

The coating with one or more vanadium-containing hydroxide, oxide hydrate and/or oxide layers can be carried out either by wet-chemical methods or via sol-gel processes, the precipitation is preferably carried out by wet-chemical methods. In the case of application by wet-chemical methods, coating with the corresponding vanadium-containing oxides, hydroxides and/or oxide hydrates takes place. To this end, the substrates are suspended in a solvent or solvent mixture, preferably water, and solutions of the metal salts suitable for the formation of hydroxide, oxide hydrate and/or oxide layers and one or more vanadium compounds are added. The pH necessary for precipitation of the respective hydroxide, oxide hydrate and/or oxide is set and optimised by methods known to the person skilled in the art.

The vanadium compounds can be introduced into the coating with the hydroxide, oxide hydrate and/or oxide layers at any point in time and in any form, such as, for example, in solid form or as a solution of one or more vanadium compounds. The vanadium compounds are preferably added in the form of a solution, it being possible for this to take place via the solutions of the metal salts suitable for the formation of the hydroxide, oxide hydrate and/or oxide layers and/or via the auxiliary solutions necessary in the coating process in the setting of the coating parameters, such as, for example, pH or amount of solvent. The vanadium compounds are preferably added via the auxiliary solutions necessary for control of the pH, where the auxiliary solutions are preferably aqueous solutions of acids or bases, such as, for example, hydrochloric acid or sodium hydroxide solution. In a further embodiment, the vanadium compound can be introduced into the hydroxide, oxide hydrate and/or oxide layer in such a way that the vanadium concentration in the layer increases or decreases in the form of a gradient in the direction of the surface of the vanadium-containing layer. The gradient formation is controlled via the point in time and rate of vanadium addition. If, for example, the vanadium concentration is to increase in the direction of the surface, this can take place, for example, through specific addition of the vanadium compounds at the end of the application of the hydroxide, oxide hydrate and/or oxide layer to the substrate. The vanadium compounds here can be introduced in the auxiliary solution necessary for control of the pH, with which the precipitation of the hydroxide, oxide hydrate and/or oxide layer is completed. The desired size of the gradient can be set via control of the rate of addition. All other possibilities of gradient control which are feasible in connection with this invention are within the range of knowledge of the person skilled in the art.

Suitable vanadium compounds are in principle all vanadium compounds in various oxidation states which are soluble in a solvent or solvent mixture, for example vanadium (IV) or vanadium(V) compounds. Preference is given to the use of vanadyl(IV) salts, for example vanadyl chloride or vanadyl sulfate, vanadates or solutions of vanadium(V) oxide, in particular sodium metavanadate.

Suitable metal salts for the formation of the hydroxide, oxide hydrate and/or oxide layers are the corresponding halides, nitrates and/or sulfates, the corresponding halides and/or nitrates are preferably employed. The sulfates, phosphates and/or borates can be co-precipitated together with the oxides, hydroxides and/or oxide hydrates from suitable metal salts and from corresponding sulfate, phosphate or borate sources. Suitable sulfate sources are sulfuric acid and all soluble sulfates, such as, for example, sodium sulfate, potassium sulfate or lithium sulfate, suitable phosphate sources are phosphoric acid or all soluble phosphates, such as, for example, sodium phosphate, disodium hydrogenphosphate or potassium phosphate, and suitable borate sources are all soluble borates, such as, for example, sodium borate or sodium diborate. The amount of the sulfates, phosphates and/or borates and the precipitation conditions, such as, for example, pH or temperature, can be optimised by methods known to the person skilled in the art.

The pigments obtained in this way are subsequently calcined. The calcination can be carried out at temperatures of 300-900° C., preferably at 600-900° C. Through the calcination, the precipitated oxides, hydroxides and/or oxide hydrates are dehydrated, converted into the corresponding oxides and compacted.

In a further embodiment of the process according to the invention, an organic coating which additionally stabilises the pigments according to the invention against further weathering influences can additionally be applied to the calcined vanadium-containing oxide layer. The organic coating is applied in solution at temperatures above 60° C., preferably above 70° C. Suitable solvents are organic solvents, water or mixtures thereof, water is preferably used. The reaction time necessary for application of the organic coating is at least 5 minutes, it is preferably carried out over a period of 10 to 90 minutes, but can also be extended as desired. The pigment obtained is worked-up and isolated by methods familiar to the person skilled in the art, for example by filtration, drying and sieving.

Besides good photostability, the photostabilised effect pigments according to the invention are distinguished by good applicational properties. Through the calcination, the oxide layers are dehydrated and compacted, which results in a reduction in the porosity of the pigment surface. Less water can be absorbed on the compacted surface, and the disadvantageous effects of water adsorbed in the interfacial layer can thus be reduced in the surface coating. The calcination also removes water bound chemically in the form of hydroxides or oxide hydrates. This has advantages on use of the pigments in plastics since water present in thermoplastic polymers, such as, for example, in polyesters, can result in hydrolytic decomposition of the polymer at elevated temperatures. In the case of pigments coated with hydroxides or oxide hydrates, liberation of water can occur during plastics processing, causing initiation of the undesired degradation of the polymer chains. In the case of the pigments according to the invention, the calcination of the oxide layer means that water also cannot exit during processing of the pigments in the plastics, so that they are particularly suitable for this area of application.

Owing to the improved applicational properties, the photostabilised effect pigments described here are suitable for a multiplicity of applications. The invention thus furthermore relates to the use of the photostabilised effect pigments according to the invention for pigmenting plastics, surface coatings, such as, for example, hydrocoatings or powder coatings, paints, printing inks, cosmetic formulations, paper, ceramic materials, glasses, films, in security printing, in the agricultural sector, for example in colouring seed, for laser marking of, for example, paper or plastics, in thermal protection and for the preparation of pigment compositions, such as, for example, pearlets and pastes, and of dry preparations, such as, for example, pellets, granules, chips, etc., which are preferably used in printing inks and surface coatings. In applications in which the toxicity of the materials employed plays a part, for example in cosmetic formulations, the use of vanadium(IV) compounds for the production of the vanadium-containing oxide layers is preferred. The pigments according to the invention can be employed in a multiplicity of known binders used in colour systems and can be used both in aqueous and solvent-based systems. The pigments can be incorporated into the respective application media by all methods known to the person skilled in the art.

In the case of cosmetics, the effect pigments according to the invention are particularly suitable for products and formulations of decorative cosmetics, such as, for example, nail varnishes, colouring powders, lipsticks or eyeshadows, soaps, toothpastes, etc. The pigments according to the invention can of course also be combined in the formulations with cosmetic raw materials and assistants of any type. These include, inter alia, oils, fats, waxes, film formers, preservatives and assistants which generally determine the applicational properties, such as, for example, thickeners and rheological additives, such as, for example, bentonites, hectorites, silicon dioxide, Ca silicates, gelatine, high-molecular-weight carbohydrates and/or surface-active assistants, etc. Formulations comprising the pigments according to the invention can be of the lipophilic, hydrophilic or hydrophobic type. In the case of heterogeneous formulations having discrete aqueous and non-aqueous phases, the particles according to the invention may in each case be present in only one of the two phases or also distributed over both phases.

The pH values of the aqueous formulations can be between 1 and 14, preferably between 2 and 11 and particularly preferably between 5 and 8. The concentrations of the pigments according to the invention in the formulation are unlimited. They can be—depending on the application—between 0.001 (rinse-off products, for example shower gels) and 100% (for example lustre-effect articles for particular applications in the case of the use of effect pigments as substrate). The pigments according to the invention may furthermore also be combined with cosmetic active ingredients. Suitable active ingredients are, for example, insect repellents, UV A/BC protection filters (for example OMC, B3, MBC), anti-ageing active ingredients, vitamins and derivatives thereof (for example vitamin A, C, E, etc.), self-tanning agents (for example DHA, erythroiose, inter alia) and further cosmetic active ingredients, such as, for example, bisabolol, IPO, ectoine, emblica, allantoin, bioflavonoids and derivatives thereof.

The effect pigments according to the invention are particularly suitable for use in plastics, for example in agricultural sheeting, infrared-reflective films and sheets, gift foils, plastic containers and mouldings for all applications known to the person skilled in the art, since, particularly in plastics, the photostability of the effect pigments according to the invention results in an extension of the durability of products produced therefrom. Suitable plastics for incorporation of the effect pigments according to the invention are all common plastics, for example thermosets or thermoplastics. The possible applications and the plastics, processing methods and additives which can be employed are described, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff., the disclosure content of which is incorporated herein. The incorporation can take place into all known plastics and in all manners known to the person skilled in the art, for example purely physically by mixing and also chemically by reaction of corresponding functional groups of an organic coating that may have been applied with the plastic. In particular, the effect pigments according to the invention are suitable in applications with high input of shear energy, as is required, for example, in some plastics applications. Thus, it has, surprisingly, been found that the photostabilisation according to the invention is still present even after very intensive mechanical loading. This is due to the very strong interactions of the stabilisation agents with the decisive interference layer.

On use of the pigments in surface coatings and inks, all areas of application known to the person skilled in the art are possible, such as, for example, powder coatings, hydrocoatings, automobile paints, printing inks for gravure, offset, screen or flexographic printing, and for coatings in outdoor applications. For the preparation of printing inks, a multiplicity of binders, in particular water-soluble types, is suitable, for example based on acrylates, methacrylates, polyesters, polyurethanes, nitrocellulose, ethylcellulose, polyamide, polyvinyl butyrate, phenolic resins, maleic resins, starch or polyvinyl alcohol. The surface coatings can be water- or solvent-based coatings, where the choice of coating constituents is subject to the general knowledge of the person skilled in the art. The pigments according to the invention are preferably employed in surface coatings, such as, for example, in automobile paints or water-borne coatings, which, owing to the particular stability of the pigments, are suitable for all indoor and outdoor applications. In powder coating formulations, the effect pigments according to the invention can be incorporated simply even without further organic coating and in these applications exhibit a bright, metallic lustre with pronounced sparkle or glitter effect. On use in outdoor applications, the occurrence of chalking and greying is greatly delaying or, in highly weatherstable formulations, the so-called superdurable powder coatings, very substantially avoided. In the case of silane-based weather stabilisations known from the prior art, incompatibility with the powder coating matrix often occurs, in particular in the area of so-called dry blending, which is often evident from strong pigment associations in the baked powder coating layer. This defect is scarcely observed in the case of the effect pigments according to the invention, owing to the mainly purely inorganic weather-stabilising layer.

Owing to the broad applicability, the present invention likewise relates to plastics, paints, coatings, printing inks, cosmetic formulations, paper, ceramic materials, glasses, films, seed, pigment compositions and dry preparations comprising one or more of the photostabilised effect pigments according to the invention.

The following examples are intended to explain the invention in greater detail, but without limiting it.

EXAMPLES

Determination of the Photoactivity:

The pigment samples were incorporated into a plastic matrix, and the extent of reduction of $Pb^{2+}$ to Pb was determined visually. The assessment of the grey coloration is carried out in accordance with ISO 105-Part A $O_2$ (corresponds to DIN 54 001). The test scale extends from 5 (very good) to 1 (very poor).

Comparative Example 1

100 g of mica flakes having a particle size of 10-50 µm are suspended in 1 l of water and heated to 75° C. with stirring. An aqueous 10% solution of 3.35 g of $SnCl_4$ is metered into the suspension over the course of one hour, during which the pH is held at 1.8 by addition of 32% sodium hydroxide solution. After a subsequent stirring time of 30 minutes, an aqueous 30% solution of 237 g of $TiCl_4$ is metered in over the course of 12 hours, during which the pH is held at 1.8 by addition of 32% sodium hydroxide solution. The mixture is subsequently stirred for a further 30 min, and the pH is adjusted to 4.0 using sodium hydroxide solution. The resultant intermediate comprises about 2% of tin oxide and 100% of titanium dioxide, based on the mica content.

The pigment is separated off from the supernatant by filtration washed. After drying at 120° C., the pigment is calcined at 800° C. for 45 min, and the resultant effect pigment having a blue interference colour is freed from coarse fractions by sieving (mesh width 63 µm).

The photoactivity of this pigment is assessed as 1.

Example 1

The vanadium-containing pigment is prepared as described in Comparative Example 1, With 64 mg of sodium vanadate * $4H_2O$ being added the sodium hydroxide solution used to keep the pH constant during the formation of the $TiO_2$ layer.

The pigment thus comprises a doping of 0.03% of vanadium(V) oxide, based on the total weight.

The photoactivity of this pigment is assessed as 3.

Example 2

The base pigment suspension is prepared as described in Comparative Example 1. The pH is subsequently adjusted to 6.5 using sodium hydroxide solution. A solution of 3.35 g of zinc chloride in 60 ml of water is added over the course of one hour, during which the pH is kept constant using 5% sodium hydroxide solution in which 53 mg of sodium vanadate was dissolved. The pigment is worked up as described in Comparative Example 1. The pigment thus comprises by calculation 2% of zinc oxide and 0.025% of vanadium oxide, based on the total weight.

The photoactivity of this pigment is assessed as 4.

Example 3

The pigment suspension is basically prepared as described in Comparative Example 1. After the coating, the pH of the suspension is adjusted to 5.0 using sodium hydroxide solution. A solution of 9.5 g of aluminium chloride * $6H_2O$ in 100 ml of water is added over the course of one hour, during which the pH is kept constant using 5% sodium hydroxide solution in which 100 mg of vanadium(V) oxide were dissolved. The pigment is worked up as described in Comparative Example 1.

The pigment thus comprises by calculation 2% of aluminium oxide and 0.1% of vanadium oxide, based on the total weight. The mass tone of the pigment is yellowish.

The photoactivity of this pigment is assessed as 3-4.

Example 4

The pigment suspension is basically prepared as described in Comparative Example 1. During the first 75% of the coating, the pH is kept constant using 32% sodium hydroxide solution. 64 mg of sodium vanadate are dissolved in the sodium hydroxide solution used for the remaining coating. The pigment is worked up as described in Comparative Example 1. The pigment thus comprises by calculation 0.025% of vanadium oxide, based on the total weight. Owing to the preparation conditions, the doping takes place in the form of a gradient and principally in the outer $TiO_2$ layer. The photoactivity of this pigment is assessed as 3-4.

Example 5

100 g of freshly prepared, i.e. still uncalcined, silicon dioxide flakes coated with 4.0% of tin dioxide and 62% of rutile are provided in the mother liquor after the coating with a post-coating of vanadium oxide and zirconium oxide. An aqueous 5% solution of 5.23 g of $ZrOCl_2*8H_2O$ is metered with vigorous stirring over the course of one hour into the suspension (volume about 1.5 l) adjusted to pH 3.0 using sodium hydroxide solution and held at a temperature of 75° C., during which the pH is kept constant by addition of 5% sodium hydroxide solution. 32 mg of $NH_4VO_4$ had previously been added to the sodium hydroxide solution. After a subsequent stirring time of 30 minutes, the pH is adjusted to 4.0 using sodium hydroxide solution, and the effect pigment is separated off from the supernatant by filtration and washed. After drying at 120° C., calcination is carried out at 800° C. for 45 min, and the pigment having a green-gold interference colour is freed from coarse fractions by sieving (mesh width 63 μm).

The photoactivity of the pigment is assessed as 3-4.

Example 6

The vanadium-containing pigment is prepared as described in Comparative Example 1, where 54 mg of vanadyl(IV) sulfate are dissolved in the $TiCl_4$ solution.

The pigment thus comprises a doping of 0.03% of vanadium (calculated as $V_2O_5$), based on the total weight.

The photoactivity of this pigment is assessed as 3.

The invention claimed is:

1. Photostabilized effect pigment, comprising a substrate to which one or more calcined vanadium-containing oxide layers, alone or mixed with sulfates, borates or phosphates, have been applied, wherein the substrate is a flake-form or needle-shaped support and/or a flake-form or needle-shaped support coated with one or more transparent, semitransparent and/or opaque layers comprising metal oxides, metal oxide hydrates, metal suboxides, metals, metal fluorides, metal nitrides, metal oxynitrides or a mixture thereof and wherein the vanadium-containing oxide layers have a vanadium content of 0.002 to 0.2% by weight calculated as $V_2O_5$ based on the pigment as a whole, and wherein the calcined and vanadium-containing oxide layer comprises titanium oxide or the substrate is titanium oxide or a titanium oxide-containing substrate.

2. Photostabilized effect pigment according to claim 1, wherein a calcined vanadium-containing oxide layer consists of oxides of Al, Ca, Sr, Zn, Si, Zr, Ce, or Ti or a mixture thereof.

3. Photostabilized effect pigment according to claim 1, wherein the vanadium-containing oxide layer has a vanadium concentration which increases or decreases in the form of a gradient in a direction of a surface of the vanadium-containing oxide layer.

4. Photostabilized effect pigment according to claim 1, to which an organic coating has been applied to the calcined vanadium-containing oxide layer.

5. Photostabilized effect pigment according to claim 1, wherein the calcined and vanadium-containing oxide layer comprises titanium oxide.

6. Photostabilized effect pigment according to claim 5, wherein the vanadium-containing oxide layer has a vanadium concentration which increases or decreases in the form of a gradient in a direction of a surface of the vanadium-containing oxide layer.

7. Photostabilized effect pigment according to claim 1, wherein the vanadium-containing oxide layers have a vanadium content of 0.01 to less than 0.1% by weight calculated as $V_2O_5$ based on the pigment as a whole.

8. A process for preparing a photostabilized effect pigment according to claim 1, comprising applying one or more vanadium-containing hydroxide, oxide hydrate and/or oxide layers, alone or mixed with sulfates, phosphates and/or borates, to a substrate and subsequently calcining the pigment, wherein the substrate is a flake-form or needle-shaped support and/or a flake-form or needle-shaped support coated with one or more transparent, semitransparent and/or opaque layers comprising metal oxides, metal oxide hydrates, metal suboxides, metals, metal fluorides, metal nitrides, metal oxynitrides or a mixture thereof and wherein the vanadium containing oxide layers have a vanadium content of 0.002 to 0.2% by weight calculated as $V_2O_5$ based on the pigment as a whole.

9. A process according to claim 8, wherein the hydroxide, oxide hydrate and/or oxide layers are applied by a wet-chemical method and/or by a sol-gel process.

10. A process according to claim 8, wherein a vanadium compound is introduced into the hydroxide, oxide hydrate and/or oxide layer to provide for a vanadium concentration, in such a way that the vanadium concentration in the layer increases or decreases in the form of a gradient in a direction of a surface of the vanadium-containing layer.

11. A process according to claim 8, wherein the calcination is carried out at a temperature of 300 to 900° C.

12. A process according to claim 8, further comprising applying an organic coating to the calcined vanadium-containing oxide layer.

13. A plastic, paint, coating, printing ink, cosmetic formulation, paper, ceramic material, glass, film, seed, pigment composition or dry preparation comprising one or more photostabilized effect pigments according to claim 1.

14. Photostabilized effect pigment, comprising a substrate to which one or more calcined vanadium-containing oxide layers, alone or mixed with sulfates, borates or phosphates, have been applied, wherein the substrate is titanium oxide or a titanium oxide-containing substrate based on a flake-form or needle-shaped support coated with one or more transparent, semitransparent and/or opaque layers comprising metal oxides, metal oxide hydrates, metal suboxides, metals, metal fluorides, metal nitrides, metal oxynitrides or a mixture thereof, and wherein the vanadium-containing oxide layers have a vanadium content of 0.002 to 0.2% by weight calculated as $V_2O_5$ based on the pigment as a whole.

15. Photostabilized effect pigment according to claim 14, having an outer layer which comprises titanium oxide.

16. Photostabilized effect pigment according to claim 14, wherein a calcined vanadium-containing oxide layer consists of oxides of Al, Ca, Sr, Zn, Si, Zr, Ce, or Ti or a mixture thereof.

17. Photostabilized effect pigment according to claim 14, wherein the vanadium-containing oxide layer has a vanadium concentration which increases or decreases in the form of a gradient in a direction of a surface of the vanadium-containing oxide layer.

18. Photostabilized effect pigment according to claim 14, to which an organic coating has been applied to the calcined vanadium-containing oxide layer.

19. Photostabilized effect pigment according to claim 14, wherein the vanadium-containing oxide layers have a vanadium content of 0.01 to less than 0.1% by weight calculated as $V_2O_5$ based on the pigment as a whole.

20. A plastic, paint, coating, printing ink, cosmetic formulation, paper, ceramic material, glass, film, seed, pigment composition or dry preparation comprising one or more photostabilized effect pigments according to claim 14.

* * * * *